United States Patent
Gruber et al.

(10) Patent No.: US 10,603,280 B2
(45) Date of Patent: *Mar. 31, 2020

(54) ACTIVE INGREDIENT CONTAINING STABILISED SOLID MEDICINAL FORMS AND METHODS FOR THE PRODUCTION THEREOF

(71) Applicant: Losan Pharma GmbH, Neuenburg (DE)

(72) Inventors: Peter Gruber, Merzhausen (DE); Dirk Spickermann, Staufen (DE)

(73) Assignee: Losan Pharma GmbH, Neuenburg (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/213,655

(22) Filed: Dec. 7, 2018

(65) Prior Publication Data

US 2019/0105273 A1 Apr. 11, 2019

Related U.S. Application Data

(63) Continuation of application No. 15/705,599, filed on Sep. 15, 2017, now Pat. No. 10,206,879, which is a continuation of application No. 12/441,629, filed as application No. PCT/EP2007/008006 on Sep. 14, 2007, now Pat. No. 9,775,807.

(30) Foreign Application Priority Data

Sep. 25, 2006 (EP) .................... 06020008

(51) Int. Cl.
*A61K 9/20* (2006.01)
*A61K 9/16* (2006.01)

(52) U.S. Cl.
CPC .......... *A61K 9/2009* (2013.01); *A61K 9/1611* (2013.01)

(58) Field of Classification Search
None
See application file for complete search history.

(56) References Cited

U.S. PATENT DOCUMENTS

| | | | |
|---|---|---|---|
| 4,537,887 A | 8/1985 | Rooke et al. | |
| 5,178,878 A | 1/1993 | Wehling et al. | |
| 5,437,874 A | 8/1995 | Bru | |
| 5,567,437 A | 10/1996 | Bru-Magniez et al. | |
| 5,756,123 A | 5/1998 | Yamamoto | |
| 5,794,781 A | 8/1998 | Roulin | |
| 5,869,102 A | 2/1999 | Stroppolo et al. | |
| 8,186,506 B2 | 5/2012 | Kanios et al. | |
| 9,775,807 B2 | 10/2017 | Gruber et al. | |
| 2002/0076437 A1 | 6/2002 | Kothari et al. | |
| 2003/0100595 A1 | 5/2003 | Karim et al. | |
| 2004/0265380 A1 | 12/2004 | Delmas et al. | |
| 2006/0014832 A1 | 1/2006 | Breitenbach et al. | |
| 2018/0000739 A1 | 1/2018 | Gruber et al. | |

FOREIGN PATENT DOCUMENTS

| | | |
|---|---|---|
| DE | 199 62 251 | 9/2001 |
| EP | 0 049 061 A1 | 4/1982 |
| EP | 0 643 986 A1 | 3/1995 |
| FR | 2 670 675 A1 | 6/1992 |
| JP | 08-073399 A | 3/1996 |
| WO | WO 1993/13760 | 7/1993 |
| WO | WO 1996/07601 | 3/1996 |
| WO | WO 1997/17960 | 5/1997 |
| WO | WO 1999/19011 A1 | 4/1999 |
| WO | WO 2004/004754 | 1/2004 |

OTHER PUBLICATIONS

Larry L. Augsburger, Ph.D. "Tablets and Capsules: Design and Formulation", *PHAR 535: Pharmaceutics*, Spring, 2003. See in particular page 68. http://faculty.ksu.edu.sa/Diaa/Documents/tablet%20and%20capsules.pdf.
Freund, Sangyo KK, "Desiccant prodn. -by heating deliquescent mixt. of calcium-, magnesium-, and lithium chloride(s) sodium hydroxide, aq. binder and/ inorganic cpd", Derwent (Jan. 1983)—Abstract only.
Umagoe, O. et al. "Manufacture of Magnesium Chloride Anhydride for Desiccant", Chemical Abstracts + Indexes, American Chemical Society, vol. 109 (18), pp. 177 (Oct. 1988)—Abstract only.
*Römpp-Lexikon Chemie*, Ed. Jürgen Falbe et al., Stuttgart, vol. 10, 1998, pp. 2484-2486.
*Hunnius Pharmazeutisches Wörterbuch*, Ed. Von Artur Burger et al., Walter de Gruvter, New York, 1998, p. 336.
*Die Tablette: Handbuch der Entwicklung, Herstellung and Qualitätssicherung*, Wolfgang A. Ritschel and Annette Bauer-Brandl, Editio Cantor Verlag Aulendorf, 2002, pp. 284-288 and 364-365.
*Organikum: Organisch-chemisches Grundpraktikum*, Heinz Becker, VEB Deutscher Verlag der Wissenschaften, Berlin, 1988, pp. 24-29.
*Pharmaceutical Dosage Forms: Tablets* (vol. 1), $2^{nd}$ edition, Herbert A. Lieberman et al., editors, Marcel Dekker, Inc., New York, 1989, pp. 285-328.
*Handbook of Pharmaceutical Excipients*, Arthur H. Kibbe, Ph.D., editor, American Pharmaceutical Association, Washington, D.C., 1986, pp. 102-106.
*European Pharmacopoeia*, $3^{rd}$ Edition, Council of Europe, 1996, excerpt monographs for: saccharin sodium (1997:0787), determination of water (2.5.12), and loss on drying (2.2.32).
*European Pharmacopoeia*, Supplement to the $3^{rd}$ Edition, Council of Europe, 1999, excerpt monograph for carbasalate calcium (1998:1185).

(Continued)

*Primary Examiner* — Patricia Duffy
*Assistant Examiner* — Garen Gotfredson
(74) *Attorney, Agent, or Firm* — Chalin A. Smith; Smith Patent, LLC

(57) ABSTRACT

The invention relates to solid medicinal forms containing at least one active ingredient and at least one pharmaceutically compatible, water soluble drying agent which is selected from the group consisting of trimagnesium dicitrate and/or calcium chloride, the solid medicinal form having a drying loss of at most 6% and a relative equilibrium moisture content of 25% or less. The invention also relates to solid medicinal forms containing a moisture-sensitive active ingredient and trimagnesium dicitrate.

11 Claims, No Drawings

(56) References Cited

OTHER PUBLICATIONS

*The United States Pharmacopeia: The National Formulary*, 23rd Edition, United States Pharmacopeial Convention, Inc., Rockville, MD, 1995, excerpt monographs for: metoclopramide hydrochloride, povidone, citric acid, lactose (anhydrous and monohydrate), sodium bicarbonate, potassium benzoate, aspartame, water determination (9211), and loss on drying (731).

*The United States Pharmacopeia: The National Formulary*, 24th Edition, United States Pharmacopeial Convention, Inc., Rockville, MD, 2000, excerpt monographs for: magnesium citrate (p. 1003) and loss on drying (p. 1954).

Product brochure for Quali-V® HPMC capsules, Qualicaps LLC, 2017. http://qualicaps.com/Capsules/pharma/quali-v.

Technical Reference File for Vcaps®Plus: Hypromellose Capsules, Capsugel®, 4th edition (Mar. 2014).

ACTIVE INGREDIENT CONTAINING STABILISED SOLID MEDICINAL FORMS AND METHODS FOR THE PRODUCTION THEREOF

PRIORITY

This application is a continuation of U.S. Ser. No. 15/705,599 filed Sep. 15, 2017, which, in turn is a continuation of U.S. Ser. No. 12/441,629 filed Mar. 17, 2009, now U.S. Pat. No. 9,775,807 issued Oct. 3, 2017, which, in turn, corresponds to the national phase of International Application No. PCT/EP2007/008006 filed Sep. 14, 2007 which, in turn, claims priority to European Patent Application No. 06.020008.6 filed Sep. 25, 2006, the contents of which are incorporated by reference herein in their entirety.

FIELD OF THE PRESENT INVENTION

The present invention relates to solid medicinal forms containing at least one active ingredient and at least one pharmaceutically compatible, water soluble drying agent which is selected from the group consisting of trimagnesium dicitrate and/or calcium chloride, the solid medicinal form having a drying loss of at most 6% and a relative equilibrium moisture content of 25% or less. The invention also relates to solid medicinal forms containing a moisture-sensitive active ingredient and trimagnesium dicitrate.

BACKGROUND OF THE PRESENT INVENTION

The stability of solid medicinal forms or solid food supplement forms must be ensured during the entire life thereof. The term stability comprises the chemical stability of the active ingredient and also the physico-technical properties, such as flowability, freedom from agglomerates, splittability of tablets, and very important aspects, such as appearance, avoidance of change in color of the product and in particular taste which is very important for e.g. lozenges, chewable tablets or forms, such as effervescent tablets or drinking granules, which are to be dissolved before being applied. In the pharmaceutical field, the chemical stability over the entire life of the preparation is extremely important since the active ingredient content shall not be reduced, if possible, and also the formation of disintegration products which may be quite toxic shall be avoided to the greatest possible extent.

Along with oxygen, in particular water which every active ingredient and every excipient contain in different amounts, is responsible for all kinds of stability, such as chemical stability, stability towards change in color, stability of flavor.

The person skilled in the art is familiar with a plurality of possibilities of how to ensure, or at least improve, the stability within said wide scope. Thus, it is quite common to store certain, highly sensitive medicinal products in a deep-freezer, e.g. at −15 to −25° C., or at least in a refrigerator prior to the application thereof. This measure extremely limits the applicability and markedly raises the cost for the medicinal product.

The measure of drying the active ingredients and, where appropriate, also all excipients linked with the active ingredients prior to the production of the solid forms is widespread. However, partially tremendous problems occur in this connection. Dried powders or granules, for example, show extreme electrostatic charges. They thus lose their flowability and, on production machines, cannot be filled into capsules or sachets, for example. The bond resulting when tablets are compressed is impossible without the involvement of water. Therefore, no tablets which have sufficient mechanical stability can be produced from over-dried granules. Every thermal drying process implies the danger of an already starting disintegration of the sensitive active ingredient.

Finally, the person skilled in the art has the possibility of drying said solid forms after the production. However, this also creates problems since e.g. dried capsules and tablets can be electrostatically charged and can no longer be filled in trouble-free manner into the containers by high-speed packaging machines. Hard gelatin capsules, for example, lose their flexibility and are also electrostatically charged after drying and cannot be filled under the aspects of an efficient pharmaceutical production.

However, here, too, the person skilled in the art ultimately has the possibility of filling the solid forms into containers such as tightly sealed glass vials or bottles, polyethylene (PE) cans or aluminum tubes and provide them with a dry plug containing a suitable drying agent, such as silica gel or molecular sieve. However, this ultimate possibility of stabilizing moisture-sensitive solid forms also has numerous drawbacks. Such vials are usually refused by patients since their handling is much more impractical than that of blister strips. The dry plug in itself is an expensive component of packaging means and the drying agent in the plug only has a limited intake capacity. For example, when 50 or 100 tablets having an individual weight of 500 mg are filled, the dry plug cannot extract the amount of water necessary to stabilize the product from the tablets and absorb it. In particular in the case of very sensitive active ingredients, the greatest drawback is, however, that the drying of the solid form in the sealed packaging means usually takes weeks and the moisture-sensitive active ingredient is already excessively disintegrated during this period. In addition, as shown in the course of the invention, there is an extreme gradient of the drying of the solid forms as a function of the distance of the solid form from the dry plug. Thus, tablets or capsules are usually overdried in the vicinity of the dry plug and solid forms which are disposed farther away are insufficiently stabilized by an inadequate extraction of water. This problem cannot be solved even if instead of a dry plug a dry capsule is added to the product as such between the filled tablets, e.g. in a vial or bottle.

A last possibility—in particular for active ingredients highly sensitive with respect to moisture—would consist of drying said solid forms and, where appropriate, manually filling them into sealed packaging means (on account of electrostatic charges) in rooms having a relative humidity <10%, preferably <5%, so that the product highly hygroscopic due to drying has no possibility of absorbing greater amounts of moisture endangering the stability of the product. Such a production can only be carried out in individual cases, e.g. in the production of freeze-dried products which are very expensive. It is very expensive to ensure said climatic conditions in production rooms, and it is not acceptable to burden the staff for hours, even under these extremely dry conditions.

Said problems can be overcome in individual cases by mixing the solid form with the drying agent silica (e.g. Syloid AL 1, trade name). Syloid is generally known as a drying agent and can firmly bond some percents of water under the condition of 25° C./10% relative humidity. In other words this means that the mixed-in silica extracts water e.g. from the granule constituents or tablet constituents (including the active ingredient), and directly absorbs it.

However, silica has the major drawback of being an extremely fine, dusty product usually having a particle size of some few micrometers so that it is known to be used as a flow regulator. It is insoluble in water and, when several percents are admixed to the solid form, the mixture is not compressible. The bond strength of water is already strongly reduced at 40° C. so that only disappointing results are obtained when the world-wide applicable guidelines for the stress stability tests in the pharmaceutical field (40° C., 75% relative humidity) are applied.

Classical drying agents, such as phosphorus pentoxide, calcium oxide, calcium sulfate, silica gel, are excluded for various reasons. Phosphorus pentoxide and calcium oxide are much too aggressive and together with numerous active ingredients and excipients result in incompatibilities. Calcium sulfate and silica gel are insoluble and is disappointing in particular with respect to the strength of the water bond at 40° C. Molecular sieve would be an internal drying agent suitable to only a limited extent; however, it is not permitted for oral purposes and would also have no sufficient compression properties and is insoluble.

SUMMARY OF THE PRESENT INVENTION

Therefore, it is one object of the present invention to provide a solid medicinal form which is storage-stable and suitable for active ingredients that are very sensitive to moisture.

This object is achieved by the subject matter of the claims.

It has surprisingly been found that by using certain water soluble drying agents that do not only have a high drying capacity but can also firmly bond water, it is possible to produce solid medicinal forms having excellent storage stability. In particular, moisture-sensitive active ingredients show a very good stability in the medicinal forms according to the invention.

For example, the results of the test with amoxicilline trihydrate (see Example 2) which prove that dried trimagnesium dicitrate has a bonding tendency for water higher than that of the known drying agent silica gel, are fully surprising to the person skilled in the art. Contrary to silica gel, dried trimagnesium dicitrate can bond the entire water of crystallization of amoxicilline trihydrate. Due to this test, it has been proved specifically that dried trimagnesium dicitrate mixed into a solid form can bond relatively great amounts of water and dry the constituents of this mixture, in particular a moisture-sensitive active ingredient so as to largely avoid a disintegration caused by water of the active ingredient. It was also possible to obtain very favorable results with calcium chloride.

Therefore, the invention relates to a solid composition, preferably a solid medicinal form, containing at least one active ingredient and at least one pharmaceutically compatible, water soluble drying agent, which is selected from trimagnesium dicitrate, calcium chloride and combinations thereof, characterized in that the solid composition has a drying loss, measured at 120° C./30 min, of at most 6% and a relative equilibrium moisture content, measured at 25° C., of 25% or less.

The preferred drying agents according to the present invention have the following properties:

They are physiologically harmless, cost-effective and world-wide accepted in the pharmaceutical and foodstuff fields;
water soluble, have no bad taste in the amounts used;
available and well processable with respect to production technology within a mean grain size range of 0.02 to 2.5 mm;
compressible without any problems, compactable;
chemically compatible with a plurality of active ingredients, in particular with moisture-sensitive active ingredients, such as acetylsalicylic acid (ASS), clavulanic acid, proton pump inhibitors, such as omeprazole, lansoprazole, pantoprazole and numerous moisture-sensitive prodrugs.

They have virtually no negative influence on the release rate of active ingredients from said solid forms;
the highest and firmest possible adsorbability of water in the range of up to 25% relative humidity and a temperature of at most 40° C.;
a pH of 5 to 8, preferably 5.5 to 7.5, as the 0.1 molar solution.

Suitable drying agents are calcium chloride, magnesium sulfate, tricalcium citrate, carnitine. However, to the skilled person's surprise, trimagnesium dicitrate is the best to comply with the above mentioned preferred properties of an internal drying agent. It is an inexpensive, physiologically fully harmless, water soluble salt having sufficiently good compression and compacting properties. Both the 12-hydrate and the 9-hydrate and a dried form are known.

The salt is available in both micronized form having a mean grain size of 25 µm and a mean grain size of 1 to 2 mm.

The medicinal form according to the invention has a drying loss of at most 6%, preferably of at most 4.5%, more preferably at most 3.5%, even more preferably at most 3.0%, most preferably 2.5% or less, e.g. 0.1% to 2.5% or 0.5% to 2.5%.

The drying loss is a measure of the amount of water in a solid form:

$$\text{drying loss in \%} = \frac{\text{mass of the water in the sample}}{\text{total mass of the sample}} \times 100$$

In order to determine the drying loss of a sample (e.g. a solid medicinal form), the sample is spread over a so-called drying balance and (e.g. by an accurately working infrared radiator) adjusted to the desired temperature, e.g. of 105° C. After a certain time (e.g. after 20 or 30 minutes), the drying loss due to the evaporation of water is directly read off the balance in percent. Unless otherwise specified in this application, the expression "drying loss" refers to the drying loss determined under the conditions of 105° C./30 min. A suitable device for measuring of the drying loss is the Moisture Analyzer HR83 of Mettler-Toledo company (CH-8606 Greifensee, Switzerland). The device or the drying balance is preferably used in a closed interior having an ambient temperature of 20° C. and 20% relative humidity.

The drying loss is silent on the strength of the water bond and does not permit a statement on how strongly and in what form the water is bonded. Theoretically there is retained water, capillary water, swelling water, absorbed water and water of crystallization. The former is not bonded and readily evaporates, the water of crystallization can be bonded very firmly and requires a high temperature and a long drying time for the determination of the drying loss.

In connection with the present invention it is, however, very important to have a method furnishing information on the bonding mechanism of water and the strength of the water bond. For this purpose, the so-called "relative equilibrium moisture content" (hereinafter also abbreviated as "equilibrium moisture content") is measured which forms on the sample in a fully sealed measuring cell at a certain temperature. It is also referred to as equilibrium activity or water activity. The water activity describes the bond strength of water to the active ingredient and/or the individual components of the active ingredient mixture. The measured value for the water activity and/or for the equilibrium moisture (Equilibrium Relative Humidity) has a decisive influence on the chemical stability of a moisture-sensitive active ingredient which is embedded in a solid form, such as granules, a capsule or tablet.

The equilibrium moisture content is the value of the relative humidity in which a hygroscopic product can be stored without a net moisture exchange taking place between the product and its environment. Thus, if a solid form has an equilibrium moisture content of 10% and is stored at a relative humidity of 15%, it absorbs water from its environment, if the relative moisture of the environment is below 10%, the solid form releases water to its environment and becomes even drier.

The correlation between the equilibrium moisture content and the moisture content of a solid form (drying loss) can be shown by means of the known sorption isotherm, the equilibrium moisture and/or the water activity being given on the abscissa and the water content in percent on the ordinate.

Unless otherwise specified, the equilibrium moisture content is determined as follows in a thermostatted small, tightly sealed measuring cell having a volume of about 50 ml. In the upper part of this measuring cell there is a sensor which can measure the relative moisture content resulting from the evaporation of water from the sample to be measured (the device HygroLab having the AWVC measuring cell of Rotronic company, CH 8303 Bassersdorf, Switzerland, is used). The device is officially calibrated and the measuring inaccuracy is no more than +1% relative humidity or +0.3° C. The measuring accuracy can be repeated at any time with standardized salt solutions as known to the person skilled in the art. The measurement takes place at 25° C.

If crystalline citric acid, for example, is measured with a drying loss of 0.2% (measured at 70° C./30 min), the measurement of the measuring cell thermostatted to 25° C. yields an equilibrium moisture content of 63%. However, if corn starch having a drying loss of 8.5% is measured (also determined at 70° C./measuring time 30 min), an equilibrium moisture content of only 22% can be measured. A comparison of both measuring values clearly shows that in the case of citric acid the water is only bonded very loosely in contrast to corn starch and thus is readily available for the disintegration of a moisture-sensitive active ingredient, for example.

The drying agents according to the invention which are not only strongly hygroscopic but also firmly bond the absorbed water, can suppress almost fully a disintegration caused by water or a change in color, etc., in combination with moisture-sensitive active ingredients.

The equilibrium moisture content in the solid form can be lowered by the kind and amount of the employed drying agents which is incorporated with the moisture-sensitive active ingredient into the solid form such that almost no free water is available for the disintegration of the active ingredient.

The medicinal form according to the invention has an equilibrium moisture content, measured at 25° C., of at most 25%, preferably at most 20%, more preferably at most 15%, even more preferably at most 10%, most preferably at most 6%, e.g. 1% to 6%, or 1.5% to 4% or even 1.5% to 2.5%.

The concentration of the drying agent in the medicinal form is 10 to 99.0%, preferably 15 to 75%, more preferably 20 to 50%, most preferably 30 to 40%. Unless otherwise specified, the % indications in this application referring to the concentration of substances in the solid medicinal form, are % by weight.

The concentration of the active ingredient in the medicinal form is usually 1% to 75%, more preferably 5% to 50%, even more preferably 10% to 45%, most preferably 20% to 40%, e.g. 30% to 40%.

The active ingredient can be any substance which can cause a therapeutic and/or preventive effect. The active ingredient is preferably an organic compound, i.e. a molecule containing carbon. The medicinal forms of the present invention are particularly suited for active ingredients which are sensitive to moisture (referred to as moisture-sensitive active ingredients in the present application). In the sense of the present application, an active ingredient is regarded as moisture-sensitive if a pattern of a pure active ingredient adjusted to an equilibrium moisture content of 25% at 20° C., has a disintegration of over 1% in a sealed packaging means at 40° C. within 6 months. As a function of the toxicity of the resulting disintegration product or products, the disintegration can also be up to 3%, in very rare cases up to 5%. 40° C. is the maximum stress temperature matched and harmonized world-wide in the pharmaceutical field for active ingredients and medicinal forms.

Examples of moisture-sensitive active ingredients are ASS, clavulanic acid, omeprazole and lansoprazole. The expression "active ingredient" in the sense of the present invention includes so-called prodrugs, i.e. precursors of the actually pharmacologically active substances which are not converted into one or more active metabolites in the organism until the administration thereof. Reasons for the development of a prodrug can be poor resorbability (enalaprile enalaprilate), poor solubility, a high first pass effect or high toxicity of the active substance. Prodrugs are often sensitive to moisture. They include in particular ester and amide compounds which in the presence of water tend to hydrolyze.

Therefore, the invention also relates to a solid medicinal form containing 1 to 75% by weight of moisture-sensitive active ingredient, 10 to 95% by weight of trimagnesium dicitrate and, where appropriate, further excipients. The preferred embodiments of this aspect of the invention correspond to the preferred embodiments which have been described in connection with other aspects of the invention.

The active ingredient differs from the drying agent which is also present in the medicinal form. For example, the medicinal form which includes trimagnesium dicitrate as a drying agent contains an active ingredient other than trimagnesium dicitrate and $Mg^{2+}$.

The medicinal form of the present invention is not particularly limited. It can be e.g. powder, granules, tablets, capsules or other solid forms. As to the intended use, the medicinal forms can be prepared for peroral, oral, parenteral or external application. So-called standard tablets, mini-tablets (diameter <4 mm), dragée cores, chewing tablets, orodispersible tablets, coating tablet, multi-layer tablets, retard tablets according to the coating or embedding principle, structural tablets, matrix tablets, floating tablets, bioadhesive tablets, film tablets, gastric juice resistant tablets, tablets soluble in the large intestine, effervescent tablets. These and further tablet kinds are described in "Die Tablette", W. A. Ritschel, A. Bauer-Brandl, Editio Cantor Verlag Aulendorf, 2002, whose content is herewith inserted in this application.

The medicinal form can also contain further conventional excipients, as described in "Die Tablette" W. A. Ritschel, A. Bauer-Brandl, Editio Cantor Verlag Aulendorf, 2002, whose content is herewith inserted in this application. The medicinal form can contain microcrystalline cellulose, lactose, mannitol, xylitol and disintegrants, such as cross-linked povidone or cross-linked sodium carboxymethyl cellulose. For example, silica (with the trade name of Syloid AL 1) is particularly suited as a flow regulator. Typical lubricants for the production of tablets, such as magnesium stearate and stearic acid, may also be contained. The medicinal form preferably contains microcrystalline cellulose, lactose, mannitol, xylitol, tricalciumphosphate, lubricant, flow regulator and/or sliding agents. The concentration of microcrystalline cellulose is preferably 5 to 30%, more preferably 10 to 20%, that of the lubricant is 0.3 to 2%, that of the flow regulator is 0.2 to 2.0% and that of the sliding agent is 1.0 to 5%. Finally, conventional fillers may also be contained.

Another aspect of the invention is a sealed package containing a solid medicinal form as described herein. The expression "sealed" means that the package is substantially impermeable to water. The package may have various forms. Suitable packages are e.g. the standard known packaging means, such as sachet and stick pack, produced from aluminum-coated foils, glass vials, PE or PP tubes having reliably sealing plugs or screw caps with sealing inserts. As to extremely moisture-sensitive active ingredients, an aluminum tube having a tight PE plug is particularly suited. Glass vials or bottles closed with a pilferproof closure known to the person skilled in the art have also excellently proved of value. Blister strips made of aluminum foil are possible as well.

A further aspect of the invention is a solid medicinal form according to the invention, packed in a sealed packaging means, as described above.

The solid form preferably has an equilibrium moisture content of at most 25%, preferably at most 20%, more preferably at most 15%, even more preferably at most 10%, most preferably at most 6%, e.g. 1% to 6%, or 1.5% to 4% or even 1.5% to 2.5%, each measured at 25° C., for at least 3 months, preferably for at least 6 months, preferably for at least 1 year, most preferably for the entire life of the product in the packaging means.

Along with tablets, capsules are approved embodiments of this invention. Unfortunately, hard gelatin capsules are only suited to a limited extent since the gelatine contains too much water. When the gelatine capsules are dried, they strongly embrittle, are electrostatically charged and lose their flexibility. Therefore, hydroxypropylmethyl cellulose (HPMC) capsules are preferred which basically contain markedly less water. Although the disintegration time of these capsules is somewhat prolonged, they have the advantage that even strongly dried capsules retain their flexibility.

A preferred embodiment of the present invention is thus e.g. a HPMC capsule which was filled into a glass vial having a tightly fitted plug. The filling material of the capsule consists of 30 to 40% highly moisture-sensitive active ingredient, 30 to 40% trimagnesium dicitrate, 10 to 20% dried microcrystalline cellulose, 1 to 2% lubricant and 1 to 3% sliding agent such as talcum or preferably silica. Under the severe drying condition of 120° C./30 min, the drying loss of the capsule content is 0.5 to 3.5%, preferably 1.5-3.0%, the equilibrium moisture of the content is less than 10%, preferably less than 6%. The drying loss of the HPMC capsule is 1.5 to 2.5%. However, the equilibrium moisture which has to be observed within said limits on all accounts, is very decisive.

The capsule disintegrates in water in the disintegration test, which is specified in European Pharmacopoe EP 5.0, between 6 and 12 minutes, in artificial gastric juice within 5 to 10 minutes.

If in place of the preferred drying agent trimagnesium dicitrate, calcium chloride or mixtures of both are used, the preferred weight ratios as indicated above do not change. The drying loss of the capsule content is 2 to 6 percent, the drying loss of the capsule is unchanged, each measured under equal drying conditions. The equilibrium moisture content of the capsule content is also preferably below 6%.

In the case of particularly moisture-sensitive active ingredients or in the case that relatively large amounts of moisture-sensitive active ingredient must be processed at the expense of a sufficient amount of drying agent or in the case of particularly long exposition times of the solid forms during the production and filling, the product filled in a tube or vial can also be closed with a drying agent plug in the individual case. Here, in particular dry plugs filled with the particularly active drying agent, i.e. molecular sieve, prove of value.

Another aspect of the present invention is a process for the production of a solid medicinal form. In one embodiment, the process comprises the steps of:
 a) mixing at least one active ingredient having a drying agent which is selected from the group consisting of trimagnesium dicitrate, calcium chloride and combinations thereof,
 b) where appropriate, dry granulating the composition obtained in step a) to obtain granules,
 c) compressing or encapsulating the composition obtained in step a) or the granules obtained in step b) to obtain the solid medicinal form, and
 d) where appropriate, packing the solid medicinal form into a sealed packaging agent.

In this connection, the ratio of drying agent to active ingredient in step a) should be chosen and the process be carried out under conditions such that the solid medicinal form obtained in step c) or the solid, packed medicinal form obtained in step d) has a drying loss, measured at 120° C./30 min, of at most 6% and a relative equilibrium moisture content, measured at 25° C., of 25% or less.

The preferred drying agent in the method of the invention is dried trimagnesium dicitrate. The drying agent can be dried with the active ingredient before mixing, e.g. at 100 to 150° C., preferably 110 to 140° C., most preferably 120 to 135° C. The drying time can be at least 0.5 h, preferably at least 1 h, more preferably at least 2 h, most preferably at least 3 h, e.g. 1 to 6 h, 2 to 5 h or 3 to 4 h. Alternatively, a substantially anhydrous drying agent can be used which does not have to be predried if the drying loss is at most 3.0% or less (measured at 150° C./30 min).

The maximum drying loss for calcium chloride may be at most 5.0% (measured at 150° C./30 min).

The drying agent to be used should have a drying loss of less than 3%, preferably less than 2%, most preferably less than 1%, directly before being mixed with the active ingredient. The equilibrium moisture content of the drying agent should be less than 5%, preferably less than 3%, most preferably less than 1%, directly before being mixed with the active ingredient.

The ratio of the mass of the drying agent to the mass of the active ingredient in step a) can be 0.5 to 2, preferably it is 0.75 to 1.5, most preferably 1 to 1.3.

As known to the person skilled in the art and also mentioned at the beginning, it is virtually impossible to fill or compress powder mixtures or granules having an excessively low equilibrium moisture on account of electrostatic charges or lack of compressibility (see "Die Tablette", W. A. Ritschel, A. Bauer-Brandl, Editio Cantor Verlag Aulendorf, 2002, page 286). By suitable drying agents, such as calcium chloride and preferably dried trimagnesium dicitrate, it is, however, possible, e.g. in powder mixtures, granules, tablets, etc., to realize with a moisture-sensitive active ingredient a low equilibrium moisture content such that the sensitive active ingredient is stabilized or can be inserted in solid forms at all.

This addition can be made directly before the filling of granules, for example. As a result of the avoidance of drying for the purpose of removal, electrostatic charges are avoided and the filling step in a dense packaging means, such as a stick pack or a sachet, consisting of aluminum-coated foil, is carried out. The amount of the preferred homogeneously distributed drying agent trimagnesium dicitrate is determined by the person skilled in the art such that it firmly bonds both the water absorbed during the filling step and the water present in the entire mixture such that it is no longer available for the disintegration of the active ingredient. As shown in Example 3, the ASS granule mixture in the sealed packaging means is dried by the addition of the physiologically fully harmless trimagnesium dicitrate unproblematic as regards taste such that the disintegration of the active ingredient ASS is markedly minimized. The flavors are also stabilized by the reduction of the equilibrium moisture so that along with the chemical stability of the active ingredient the sensory stability of the flavor is also markedly improved during the entire life of the preparation.

Of course, it is an advantage if in the case of highly sensitive active ingredients the production of the solid form and the filling take place under climatic control. Here, conditions of 20 to 25% relative humidity at about 20° C. (or 15 to 25 or 18 to 22° C.) have proved of value world-wide in the pharmaceutical production field. As a result of the reduced moisture in the rooms, the absorption of moisture during the working operations such as screening, mixing, tabletting and filling, is thus lowered. If the drying agents according to the invention are ignored for the work, said climatic conditions of 20% are by far not sufficient with moisture-sensitive active ingredients to guarantee a product stable for years since for reasons of stability the equilibrium moisture of the product must often be markedly below 10%. Such a product would not absorb any moisture only if in the production room the relative humidity was also below 10%.

As shown in Example 4, the highly moisture-sensitive active ingredient clavulanic acid can be excellently stabilized by the approach according to the invention. The example proves that by the addition of dried trimagnesium dicitrate the equilibrium moisture content of the mixture to be filled is only 5% (25° C.). Irrespective of this extremely low equilibrium moisture, the product can still be filled without hesitation in production rooms at 25%/20° C. The moisture inevitably absorbed during the filling step is firmly bonded by the preferred trimagnesium dicitrate and to the skilled person's surprise does not change the equilibrium moisture content of the powder mixture filled into a sealed vial. In the case of an equilibrium moisture of only 5%, the clavulanic acid is only in contact in a very small water amount so that the stability of the active ingredient can markedly be improved by the inventive measures. If as a result of complex and prolonged unavoidable production processes, the exposition times of the inventive powder mixture, granules, tablets, capsules, film tablets are extended, it is advisable to use the inventive drying agent in a coarser particle size. As a result, the water absorption of the hygroscopic drying agent is reduced due to a smaller particle surface during the exposition time. Here, particle sizes between 0.2 and 2 mm have proved of value in the case of trimagnesium dicitrate and calcium chloride, the preferred mean particle size being about 0.8 mm. However, if the active ingredient is particularly moisture-sensitive and the water inevitably introduced into the mixture by the use of excipients must be rapidly removed, the use of e.g. micronized trimagnesium dicitrate is recommended. This material has a preferred mean grain size of 0.025 mm.

In the production of solid forms having moisture-sensitive active ingredients corresponding to the invention, it is of course preferably tried to use dried excipients or excipients having a low drying loss or excipients having very firmly bonded water. Powders, granules, capsules, tablets are usually produced without moisture granulation. For this purpose, the components are mixed with the moisture-sensitive active ingredient and then filled into e.g. sealed sachets, hard gelatin capsules or are compressed into tablets. The active ingredients and the necessary excipients having a low water content are often not well flowable so that the person skilled in the art carries out dry granulation by tabletting or compacting the mixture followed by screening such that well flowable dry granules form. Basically, all excipients common in the production of granules, capsules or tablets can be used if they have a low drying loss or were predried. Predried microcrystalline cellulose, spray-dried, well tabletted lactose, mannitol, xylitol and disintegrants, such as cross-linked povidone or cross-linked sodiumcarboxymethyl cellulose are particularly suited. For example, silica (with the trade name of Syloid AL 1) is particularly suited as a flow regulator. Typical lubricants for the production of tablets, such as magnesium stearate and stearic acid, can be used without any problems since they only contain small amounts of moisture and are usually only used in an amount of 0.5%.

Another object for the person skilled in the development field is to chose along with the selection of suitable excipients the amounts of moisture-sensitive active ingredients, excipients necessary for the production process and the preferred drying agents such that powders and granules can be filled into sachets or capsules and sufficiently hard and mechanically stable tablets form which in the individual case can even be transferred into film tablets, preferably with an alcoholic coating solution. Of course, the person skilled in the art must keep an eye on the aspects, such as disintegration time of the tablets and capsules and the release rate of the active ingredient from these solid forms, for the qualitative and quantitative selection of the excipients and the preferred drying agents.

The amount to preferred drying agent must be chosen by the person skilled in the art such that
   a) after filling, an equilibrium moisture corresponding to the moisture sensitivity of the active ingredient adjusts in the solid form which has proved of value on the basis of stability investigations
   b) the moisture absorption inevitable during the production and filling operations is compensated and the stability-required equilibrium moisture content adjusts in the sealed packaging means.

Fortunately, calcium chloride and in particular trimagnesium dicitrate show a favorable processing behavior so that e.g. in the dry granulation of even maximum amounts of drying agent create no difficulties. Since both preferred excipients are also soluble in water, no problems occur with respect to the active ingredient release. As a function of the amount of moisture-sensitive active ingredient to be processed and in particular the degree of its moisture sensitivity, the solid forms consist of 10 to 99.5, preferably 15 to 75 and most preferably 20 to 50% of said drying agents.

A further aspect of the invention is the use of trimagnesium dicitrate to stabilize moisture-sensitive active ingredients or to increase the stability of moisture-sensitive active ingredients. The chemical stability of the active ingredients is preferably increased. In a particular embodiment, trimagnesium dicitrate is used to protect the active ingredient from hydrolysis.

Still another aspect of the invention is the use of trimagnesium dicitrate as a drying agent in solid medicinal forms.

Finally, the invention relates to a method for increasing the stability of moisture-sensitive active ingredients, characterized in that the active ingredient is mixed with trimagnesium dicitrate.

The latter aspects of the invention can, of course, be combined with the above described embodiments of other aspects.

DETAILED DESCRIPTION OF THE PREFERRED EMBODIMENTS

The invention is specified by the below examples without being limited thereto.

Example 1

If the preferred drying agent trimagnesium dicitrate is dried at 130° C. for several hours, a product is obtained which to the skilled person's surprise has an equilibrium moisture content having a hardly measurable value of 0.6% at 25° C.

Sodium sulfate which has a drying loss at 130° C. (testing period 30 min) of 0.06%, still yields a value of 32.7% when the equilibrium moisture content is determined. This value proves that sodium sulfate cannot adsorb either a water amount worth mentioning or firmly bonds these adsorbed amounts. This substance is fully unsuited to stabilize moisture-sensitive active ingredients.

| Tablet 1 | | | |
|---|---|---|---|
| | drying loss at 130° C./30 min | equilibrium moisture | weight increase (%) with storage at 15% relative humidity/25° C. |
| microcrystalline cellulose | 0.5 | <1.0 | 2.2 |
| trimagnesium dicitrate | 0.2 | <1.0 | 8.6 |
| calcium chloride | 0.02 | <1.0 | 45.9 |
| sorbitol | 0.1 | 9.0 | 0.1 |
| silica | 0.5 | <1.0 | 6.4 |

The substances were dried at 130° C. for 5 hours (sorbitol: 70° C.) and the drying loss was determined. Then, the weight increase of the individual substances was determined at 25° C./15% relative humidity over 27 days.

The table proves that even with a very low humidity of 15% calcium chloride can absorb major amounts of water and that to the skilled person's surprise the preferred trimagnesium dicitrate bonds more water than the generally known drying agent silica (silica gel).

Example 2

In a tightly sealing glass vessel, two Arcellas having 3.5 g trimagnesium dicitrate, dried at 130° C., or having 1.264 g amoxicilline trihydrate (water content 13.1%) are placed side by side and stored at 25° C. After 14 days, the weight of amoxicilline is only 1,105 g whereas the weight of trimagnesium dicitrate is 3.66 g. The amoxicilline released 12.6% water of crystallization which was absorbed by the drying agent. The new drying agent is active such that it virtually split off the entire water of crystallization of amoxicilline (theoretical value: 12.9%).

If this experiment is repeated with the known drying agent silica gel, the antibiotic only loses 0.1% weight after 25 days. This means that the dried trimagnesium dicitrate according to the invention represents an extremely potent drying agent.

Under precisely equal test conditions, the amoxicilline only loses 9.0% with calcium chloride dried at 130° C. after 26 days/25° C.

Example 3

Two dry mixtures having the following composition were produced:

TABLE 2

| | a) | b) |
|---|---|---|
| acetylsalicylic acid | 500 mg | 500 mg |
| sorbitol | 950 mg | 950 mg |
| citric acid | 59 mg | 59 mg |
| magnesium oxide | 25 mg | 25 mg |
| aspartame | 10 mg | 10 mg |
| lemon flavor | 25 mg | 25 mg |
| trimagnesium dicitrate | — | 125 mg |

(TOTAL 1694)

The components were mixed, filled into aluminum-coated bags and stored at 40° C. for three months.

In case a), a disintegration caused by water of acetylsalicylic acid occurred while 3.2% salicylic acid and glacial acetic acid were formed. The pattern was uneatable.

Pattern b) showed a disintegration of 0.6% and virtually no odor of glacial acetic acid. The pattern was still o.k. as regards taste.

The equilibrium moisture of pattern a) was 34% (25° C.) and that of pattern b) 8.4% due to the addition of trimagnesium dicitrate. The low equilibrium moisture according to the invention markedly stabilizes the active ingredient due to its water bond.

Example 4

Trimagnesium dicitrate, calcium chloride×2H2O are dried at 130° C. for several hours. The drying loss, measured at 150° C./30 min, is:

| Trimagnesium dicitrate: | 1.6%; equilibrium moisture content <0.5% |
|---|---|
| Calcium chloride: | 3.4%; equilibrium moisture content <0.5% |
| clavulanic acid | 3.0 kg |
| trimagnesium dicitrate (mean particle size 0.25 mm) | 4.0 kg |
| microcrystalline cellulose | 1.5 kg |
| mannitol | 1.0 kg |
| silica (Syloid AL 1) | 0.2 kg |
| povidone K25 | 0.2 kg |
| magnesium stearate | 0.1 kg |

The components were sieved in a room at 22° C., 19% relative humidity and then compacted to a slug in a roll compactor. The slug was dry granulated over 2.5 mm and 1.0 mm. The granules were kept in a sealingly closing container prior to the encapsulation.

The drying loss of the granules, measured at 105° C./30 min, was 2.4%, the equilibrium moisture content was 4.6% (25° C.). Under exactly the same conditions, the test was repeated with 3.0 kg dried calcium chloride as described above. The calcium chloride was similarly well processed into granules.

Drying loss: 1.7% (105/30 min)
Equilibrium moisture: 5.4% (25° C.)

Both granules were filled at 21° C./22% relative humidity in undried HPMC capsules (filling weight 417 mg per capsule size 1) and under the same room conditions into glass vials (20 items) and closed with sealingly closing PE plugs. Some plugs contained 2.0 g molecular sieve.

The patterns were subjected to a stress test at 40° C./75% relative humidity for 6 months.

TABLE 3

| Test parameters | Start | 3 months | 6 months | 6 months* |
|---|---|---|---|---|
| appearance capsule content | white | white | almost white | almost white |
| disintegration time capsule in water, 37° C. | 8.5 min | 9.2 min | 9.1 min | 8.8 min |
| drying loss capsule content | 2.8% | 2.6% | 2.9% | 2.5% |
| equilibrium moisture content capsule content | 5.2% | 4.8% | 5.5% | 4.2% |
| drying loss HPMC capsule | 2.7% | 2.3% | 2.2% | 2.1% |
| drying loss drying agent/plug | 1.2% | — | — | 1.6% |
| content clavulanic acid | 101.4% | 99.8% | 96.1% | 96.7% |

*pattern with dry plug
All drying losses measured at 105° C./30 min,
Drying loss drying agent/plug at 200° C./30 min Results (clavulanic acid capsules with calcium chloride):

TABLE 4

| Test parameters | start | 3 months | 6 months | 6 months* |
|---|---|---|---|---|
| appearance capsule content | white | almost white | yellow | white/yellow |
| disintegration time capsule in water, 37° C. | 7.9 min | 8.2 min | 8.6 min | 8.4 min |
| drying loss capsule content | 2.1% | 2.3% | 2.2% | 1.7% |
| equilibrium moisture content capsule content | 5.9% | 6.9% | 7.2% | 5.2% |
| drying loss HPMC capsule | 3.1% | 3.2% | 2.9% | 2.5% |
| drying loss drying agent/plug | 1.2% | — | — | 6.4% |
| content clavulanic acid | 100.7% | 98.7% | 93.1% | 94.6% |

*pattern with dry plug
All drying losses at 105° C./30 min
Drying loss drying agent/plug at 200° C./30 min Although the drying losses of the capsule content increase in both test examples due to the exposition time during the capsule filling and the water content of the undried capsule, the equilibrium moisture content of the capsule content does virtually not change in both test examples. This proves that the water absorbed during filling and extracted from the capsule is absorbed by the drying agent without the equilibrium moisture content decisive for the stability of the moisture-sensitive clavulanic acid changing. Due to the dense packaging agent, the drying losses of the capsule content and the accompanying equilibrium moisture contents hardly change during stress storage for 3 and 6 months. This is an essential precondition for the stabilization of the active ingredient. The results on the drying loss of the drying agent in the plugs are very interesting. Although the person skilled in the art knows that molecular sieve is an extremely severe drying agent, it hardly removed water from the capsules with content to the skilled person's surprise in the case of the drying agent trimagnesium dicitrate and the drying loss only increased from 1.2 to 1.6%. This is a clear evidence for the strong bond of the water to trimagnesium dicitrate. Again to the skilled person's surprise, the water absorption of the molecular sieve markedly increased from 1.2% to 6.4% in the case of the clavulane capsules with the drying agent calcium chloride. Although calcium chloride is considered a strong drying agent, the molecular sieve absorbed over 5% water from the capsules. This in turn proves that although to the skilled person's surprise trimagnesium dicitrate can bind less water than calcium chloride, the strength of the water bond is markedly higher. This makes trimagnesium dicitrate the preferred drying agent for active ingredients highly sensitive to water since the new drying agent can so to speak irreversibly bond the water up to the conditions of about 40° C. and largely dry the sensitive active ingredient by ensuring in the solid form equilibrium moisture contents around 5% up to temperatures of 40° C.

If the clavulanic acid granules are produced without one of both drying agents, they have an equilibrium moisture content of 28.9% after the production, which is an equilibrium moisture content very low for capsule granules. The active ingredient in this mixture loses, when stored at 40° C. in a sealed vial, over 25% content within one week and changes its color to light brown. Normal capsule mixtures have an equilibrium moisture content of 35 to 55%. Thus, clavulanic acid is indeed an extremely moisture-sensitive active ingredient which even in the presence of small amounts of water rapidly loses activity.

What is claimed:

1. A non-effervescent solid medicinal form comprising a hydroxypropylmethylcellulose (HPMC) capsule filled with a capsule filling comprising:
   a. 20 to 40% by weight of a moisture-sensitive active ingredient, wherein said active ingredient is not trimagnesium dicitrate;
   b. 20 to 50% by weight of trimagnesium dicitrate acting as a drying agent that stabilizes the moisture sensitive agent against hydrolysis during storage; and
   c. 5 to 30% by weight of a microcrystalline cellulose;
   wherein said medicinal form exhibits a relative equilibrium moisture, measured at 25° C., of at most 15%.

2. The non-effervescent solid medicinal form of claim 1, wherein said microcrystalline cellulose comprises 10 to 20% by weight of the capsule filling.

3. The non-effervescent solid medicinal form of claim 1, wherein said medicinal form exhibits a relative equilibrium moisture, measured at 25° C., of at most 10%.

4. The non-effervescent solid medicinal form of claim 1, wherein said capsule filling further includes 0.3 to 2% by weight of stearic acid.

5. The non-effervescent solid medicinal form of claim 1, wherein said capsule filling further includes 1 to 2% by weight of stearic acid.

6. The non-effervescent solid medicinal form of claim 1, wherein said capsule filling further includes 0.2 to 2% by weight of silica.

7. The non-effervescent solid medicinal form of claim 1, wherein said solid medicinal form is packaged together with an external drying agent in a tight packaging that is substantially impermeable to water.

8. The non-effervescent solid medicinal form of claim 1, wherein the moisture-sensitive active ingredient and the trimagnesium dicitrate drying agent are dry granulated together.

9. A non-effervescent solid medicinal form comprising a hydroxypropylmethylcellulose (HPMC) capsule filled with a capsule filling comprising:
   a. 20 to 40% by weight of a moisture-sensitive active ingredient, wherein said active ingredient is not trimagnesium dicitrate;
   b. 20 to 50% by weight of trimagnesium dicitrate acting as a drying agent that stabilizes the moisture sensitive agent against hydrolysis during storage; and
   c. 5 to 30% by weight of a microcrystalline cellulose;
   wherein the equilibrium moisture of said capsule filling, measured at 25° C., is less than 10%.

10. The non-effervescent solid medicinal form of claim 1, wherein said medicinal form exhibits a relative equilibrium moisture, measured at 25° C., of 1 to 6%.

11. The non-effervescent solid medicinal form of claim 9, wherein the equilibrium moisture of said capsule filling, measured at 25° C., is less than 6%.

\* \* \* \* \*